US005922356A

United States Patent [19]
Koseki et al.

[11] Patent Number: 5,922,356
[45] Date of Patent: Jul. 13, 1999

[54] SUSTAINED RELEASE FORMULATION

[75] Inventors: Norimasa Koseki, Nishinomiya; Akihiko Sano, Toyonaka, both of Japan

[73] Assignees: Sumitomo Pharmaceuticals Company, Limited, Osaka-fu; Koken Co., Ltd., Tokyo-to, both of Japan

[21] Appl. No.: 08/947,463

[22] Filed: Oct. 9, 1997

[30] Foreign Application Priority Data

Oct. 9, 1996 [JP] Japan ................................. 8-268801

[51] Int. Cl.⁶ ............................................. A61K 9/14
[52] U.S. Cl. .......................... 424/489; 424/468; 424/469
[58] Field of Search .................................. 424/85.1, 488, 424/489, 464, 469; 514/56

[56] References Cited

U.S. PATENT DOCUMENTS

| | | | |
|---|---|---|---|
| 4,774,091 | 9/1988 | Yamahira et al. | 424/426 |
| 4,855,134 | 8/1989 | Yamahira et al. | 424/85.7 |
| 4,864,907 | 9/1989 | Sakuria et al. | 514/56 |
| 5,236,704 | 8/1993 | Fujioka et al. | 424/85.1 |
| 5,344,644 | 9/1994 | Igari et al. | 424/85.1 |
| 5,385,738 | 1/1995 | Yamahira et al. | |
| 5,693,341 | 12/1997 | Schroeder et al. | 424/488 |

FOREIGN PATENT DOCUMENTS

| | | |
|---|---|---|
| 0 381543 | 8/1990 | European Pat. Off. |
| 0 381543A1 | 8/1990 | European Pat. Off. |
| 0 139286 | 8/1991 | European Pat. Off. |
| 0 503583A1 | 9/1992 | European Pat. Off. |
| 0 671165 | 9/1995 | European Pat. Off. |
| 0 671165A2 | 9/1995 | European Pat. Off. |
| 60-84213 | 5/1985 | Japan . |
| 60-89418 | 5/1985 | Japan . |
| 60-97918 | 5/1985 | Japan . |
| 60-112713 | 6/1985 | Japan . |
| 60-126217 | 7/1985 | Japan . |
| 61-236729 | 10/1986 | Japan . |
| 62-230729 | 10/1987 | Japan . |
| 2 710 | 1/1990 | Japan . |
| 5 71566 | 10/1993 | Japan . |

OTHER PUBLICATIONS

Murata et al., "Additive effect of chondroitin sulfate and chitosan on drug release from calcium–induced alginate gel beads," *Journal of Controlled Release*, pp. 101–108, No. 38 (1996).
B. Alberts et al., Molecular Biology of the Cell, 692–701 (1983) J. Scott, Biochem J, 252:313–323 (1988).
A.K. Garg, Biomaterials, 10:413–419 (1989).

*Primary Examiner*—Thurman K. Page
*Assistant Examiner*—William E. Benston, Jr.
*Attorney, Agent, or Firm*—Birch, Stewart, Kolasch & Birch, LLP

[57] ABSTRACT

The present invention relates to a sustained release formulation used for treatment or prevention of the diseases, which contains a therapeutically effective substance as an active ingredient, collagen as a drug carrier, and glycosaminoglycan as an additive. The formulation allows controlled release of the therapeutically effective substance.

13 Claims, 5 Drawing Sheets

FIG. 1-A
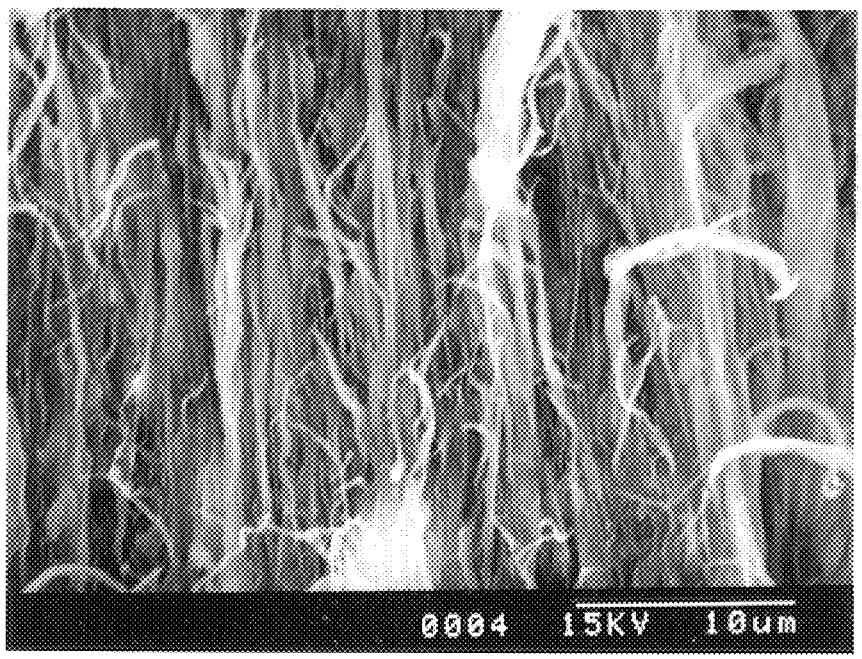
FIG. 1-B
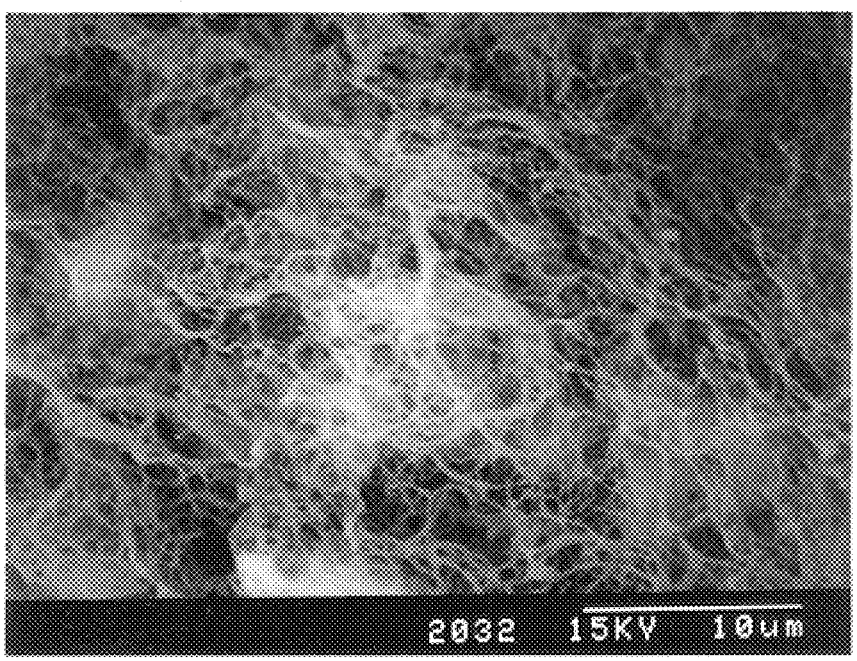

Influence of chondroitin sulfate on the release of IFN

Effect of lysozyme MP-chondroitin sulfate (3%)

FIG. 4-A
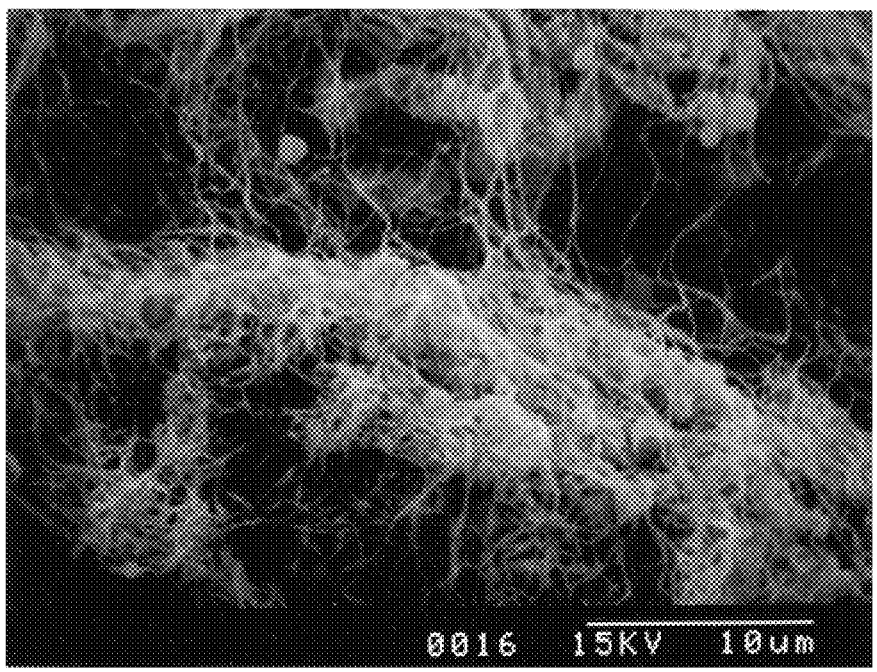
FIG. 4-B
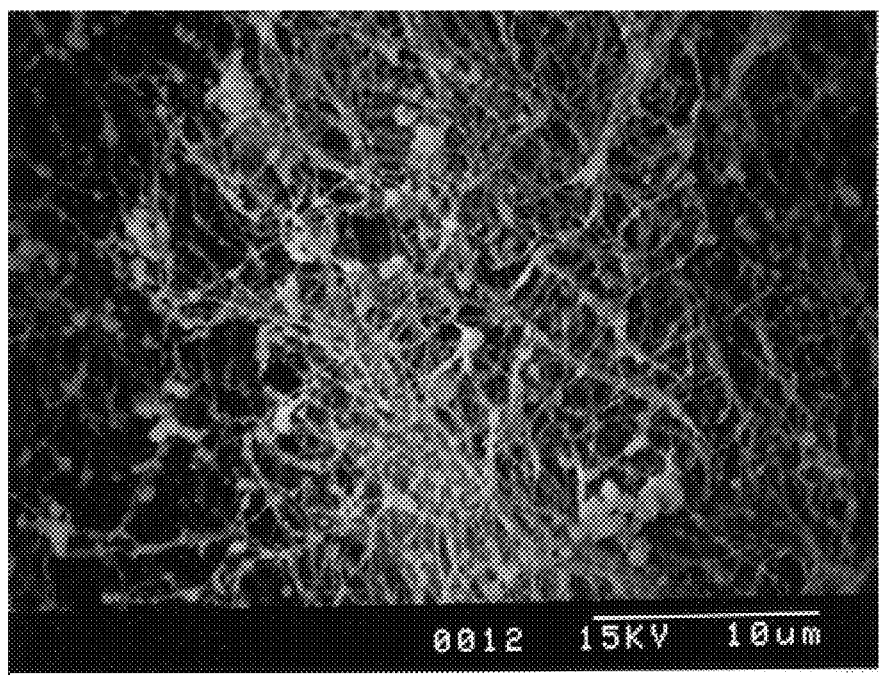

FIG. 4-C
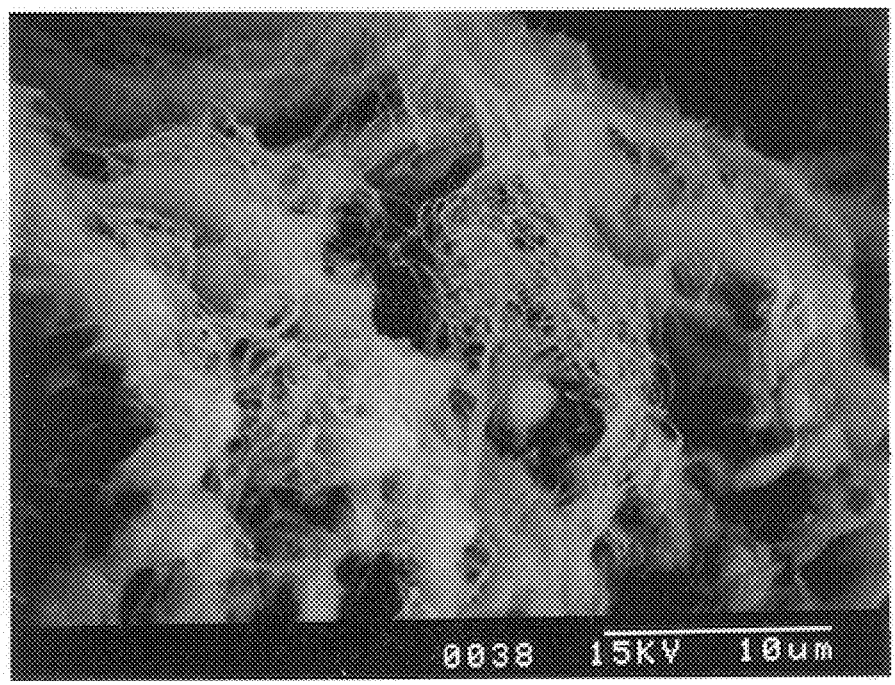
FIG. 4-D
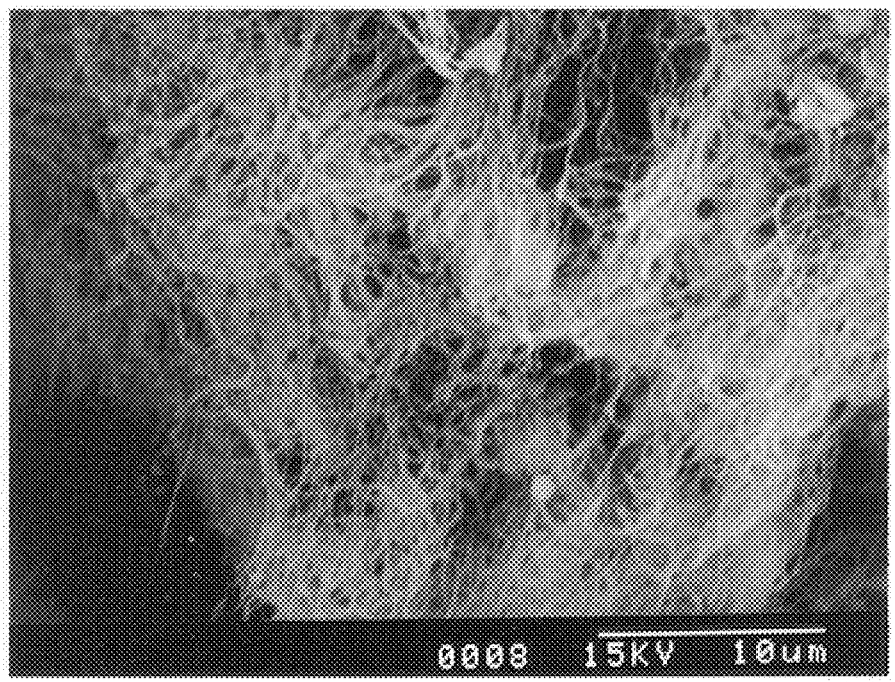

FIG. 4-E
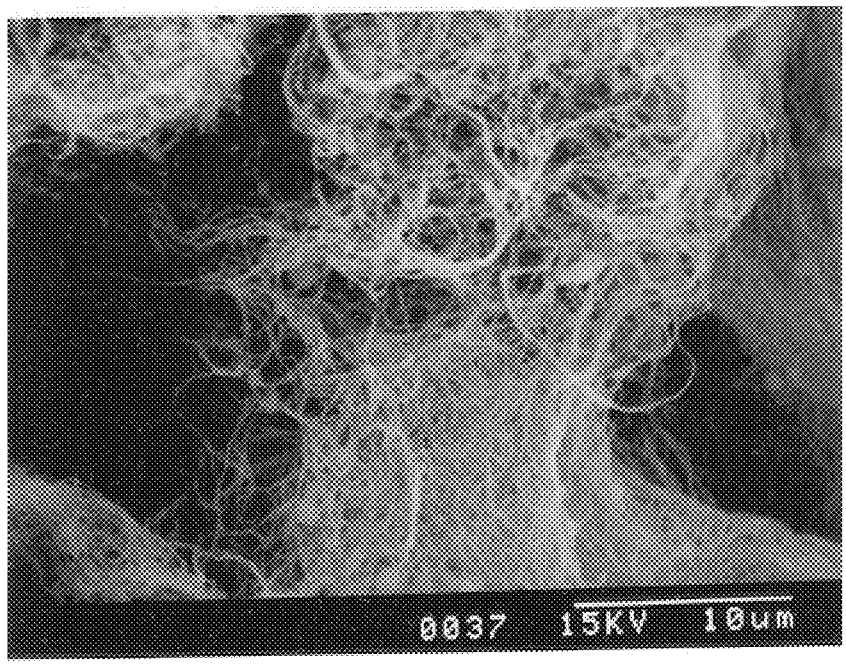
FIG. 4-F
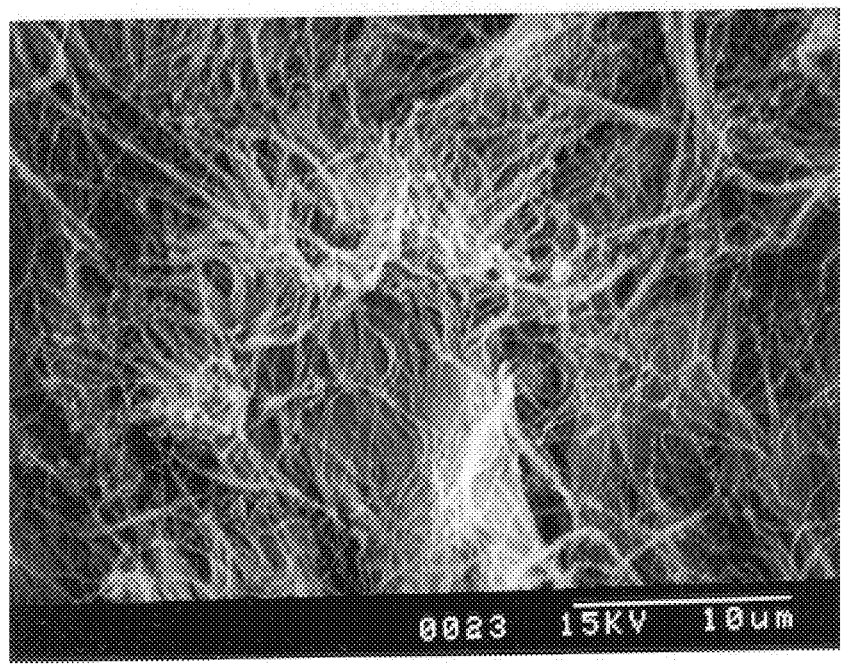

SUSTAINED RELEASE FORMULATION

FIELD OF THE INVENTION

The present invention relates to a pharmaceutical formulation used for the treatment or prevention of disease. In particular, it relates to a controlled release formulation which allows prolonged and sustained release of a drug. More particularly the present invention relates to a controlled release formulation in which glycosaminoglycan contained therein controls fiber-forming of a collagen added as a carrier, thereby releasing of a drug from the formulation is suitably controlled.

BACKGROUND OF THE INVENTION

Advantage of sustained release of an active ingredient from a pharmaceutical formulation over a long period of time has been discussed from the viewpoints of achieving an improved therapeutic effect by prolonged retention time of effective blood level, decreased side effect by suppressing the maximal blood level as low as possible, and decreasing frequency of administration to relief a pain of a patient. For this purposes the present inventors have developped a sustained release formulation containing collagen as a carrier, for which patent applications have been filed (Japanese Patent Application (Kokai) Nos. 60-126217, 60-97918, 60-84213, 60-89418, 60-112713, 61-236729, and 62-230729).

It has been demonstrated that a releasing profile of a drug from a formulation containing collagen as a carrier can be controlled by adding human serum albumin or acids such as citric acid (Japanese Patent Publication (Kokoku) No. 5-71566 and Japanese Patent Publication (Kokai) No. 2-710). In such formulation, release of an active ingredient from said formulation was controlled by changing interaction between a drug and collagen through, for example, ionic interaction. Thus, drug-release from the formulation is characterized by physico-chemical properties of serum albumin or citric acid or the amount of said additive kneaded therein, and the additive per se cannot positively alter the property of collagen so as to suitably control a drug release.

Glycosaminoglycan is a biological substance which covalently binds to a protein in organisms and exists in the form of proteoglycan. It is a component of an extracellular matrix which fills in the space between cells in a tissue similarly to collagen.

Glycosaminoglycan and collagen are also known to exert specific interactions in organisms. While collagen usually exists as a fiber-like protein in organisms, purified collagen also forms fiber when exposed to physiological conditions. However, the collagen fiber reconstituted in vitro has diameter less than 50 nm, while a collagen fiber in vivo has a diameter varying in the range from 10 to 130 nm in diameter (Molecular Biology of the Cell, 1983). It is also known that such variation in diameter mainly results from the interaction between collagen and glycosaminoglycan which exists in mesenchyme of the tissue. Actually, it has been demonstrated that, on in vitro fiber-forming experiment using collagen purified in the presence of glycosaminoglycan, fiber-forming of collagen is accelerated or suppressed depending on the type and/or the concentration of glycosaminoglycan (Biochem. J. (1988) 252, 303–323; Biomaterials (1989) 10, 413–419). In addition, collagen fiber which was reconstituted in the presence of glycosaminoglycan is formed as a finer fiber than that reconstituted in the absence of glycosaminoglycan, and the combination of collagen with glycosaminoglycan forms mesh-like structure.

In such a situation stated above, there has been a desire to develop a formulation which produces more appropriate controlled drug release.

The present inventors conducted experiments in order to obtain a controlled release formulation which can suitably control the release of an active ingredient, and eventually, found that an addition of a glycosaminoglycan including chondroitin sulfate to a sustained release formulation containing together with an active ingredient, collagen as a carrier can result in controlled release of the active ingredient. The present invention has been accomplished based on such finding.

The present invention provides a sustained formulation containing an active ingredient, collagen as a carrier, which is characterized by additionally containing one or more glycosaminoglycans as a controlled release factor.

Glycosaminoglycans used for preparing the formulation to the invention may be those having a repeated structure of disaccharides consisting of aminosugar and uronic acid or galactose, which include, for example, chondroitin sulfates such as (1a)chondroitin 6-sulfate and (1b)chondroitin 4-sulfate, (2)hyaluronic acid, (3)heparin, (4)heparan sulfate, (5)dermatan sulfate, and (6)keratan sulfate which have a formula:

(1a) Chondroitin 6-sulfate

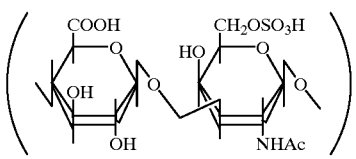

(1b) Chondroitin 4-sulfate

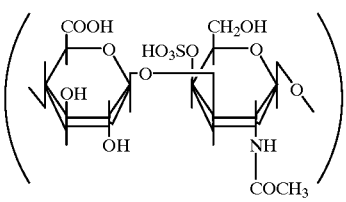

(2) Hyaluronic acid

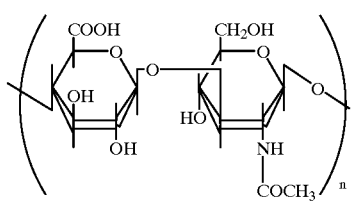

(3) Heparin

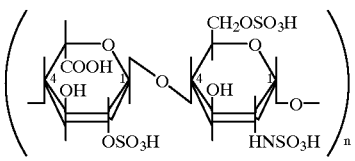

-continued (4) Heparan sulfate

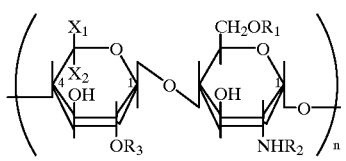

R$_1$, R$_3$ = SO$_3$H/H
R$_2$ = SO$_3$H/Ac
X$_1$ = COOH   OR   X$_1$ = H
X$_2$ = H              X$_2$ = COOH (5) Dermatan sulfate

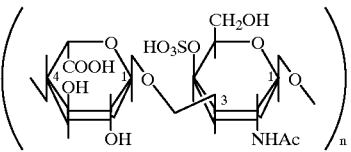

(6) Keratan sulfate

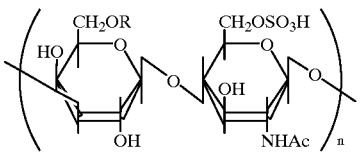

, wherein n is a positive integer.

For the purpose of controlling the release of an active ingredient from the formulation, most preferred is chondroitin sulfate.

The content of glycosaminoglycan in the formulation is preferably less than 40% by weight of the formulation, more preferably 1–10%. Collagen is preferably 20–95% by weight of the formulation, more preferably 75–91 (wt/wt)%.

Accelerated release, restricted initial release in necessary, and desired constant release of an active ingredient can be accomplished by changing the contents of these components.

Investigation of the releasing behavior of the active ingredient which is released from the formulation containing human serum albumin as an additive has demonstrated that the active ingredient is released parallel with the release of human serum albumin. To the contrary, when chondroitin sulfate was used as an additive, releasing of an active ingredient and that of chondroitin sulfate have not been closely related to each other. It was demonstrated that a part of the chondroitin sulfate remains in the formulation up to the late phase of the release, which shows that the two substances which are used as an additive have different functions on sustained release of an active ingredient.

The present invention provides a method of controlling the release of an active ingredient from the formulation by using a drug carrier which contains collagen as a main constructive component and is formed in the presence of glycosaminoglycan on the basis of the interaction between collagen and glycosaminoglycan.

The effect of the invention is substantially based on the effect of glycosaminoglycan on collagen matrix. Accordingly, a therapeutically active ingredient contained in the formulation of the invention, i.e. an active ingredient for the purpose of the treatment or prevention of diseases is not limitative and includes, for example, substances having physiological activity such as protein, peptide, glycoprotein, polysaccharide or the like, or substances such as gene, low molecular drug and so on.

Physiologically active substances belonging to protein, peptide, or glycoprotein include, for example, interferon (IFN or INF), interleukine (IL), colony-stimulating factor (CSF), macrophage-activating factor (KAF), macrophage-migration-inhibiting factor (MIF), and so on. Interferon as used herein may be alpha-, beta-, gamma-, or any other type of interferon, or a combination thereof. Similarly, interleukine may be any one of IL-1 to IL-12 which has been reported previously, colony-stimulating factor (CSF) may be whether multi-CSF, GM-CSF (granulocyte and monocyte-macrophage CSF), G-CSF (granulocyte CSF), M-CSF (monocyte-macrophage CSF) or any other type of CSF, or a combination thereof.

Representative substances having physiological activity, which belong to protein, peptide, or glycoprotein, include a hormone, for example, insulin, growth hormone (GH), pituitary hormone, sex hormone, adrenocortical hormone and the like; a growth hormone, for example, somatomegine (SM), epidermal growth factor (EGF), tumor growth factor (TGF), fibroblast growth factor (FGF), erythropoietin (EPO), platelet-derived growth factor (PDGF), insulin-like growth factor (IGF), hepatocyte growth factor (HGF) and the like; neurotrophic factor, for example, nerve growth factor (NGF), brain-derived neurotrophic factor (BDNF), NT-3, NT-4, glia cell-derived neurotrophic factor (GDNF), ciliary neurotrophic factor (CNTF), and the like; opioid, for example, endorphine, neoendorphine, dynorphine, and the like; coagulation factor, for example, factor I (i.e. fibrin), factor VIII, thrombin (i.e. a kind of protease) and the like; coagulation inhibition factor, for example, hirudin and the like which suppresses an effect of thrombin; an enzyme having fibrinolytic activity, for example, tissue plasminogen activator (t-PA), urokinase (UK) and the like; and an enzyme having bacteriolytic effect such as lysozyme.

An active ingredient used in the present an formulation, ice., biologically active protein, peptide, and glycoprotein, was illustrated in the above by categorizing to cytokine, hormone, growth factor, proliferating factor, neurotrophic factor, opioid, coagulating factor, coagulation inhibition factor, enzyme and the like. However, some of them cannot be precisely categorized because they have a variety of effects. The active ingredients of the invention are not limited to those belonging to above-noted category examples, and they can be peptide, protein, glycoprotein, and the like, which are expected to be developed as a pharmaceutical product in the future, such as enzyme inhibitors, for example, tissue inhibitor of metaloprotease (TIMP) which is a collagenase inhibitor, bone morphogenic proteins (BMP), or antibodies etc.

A gene includes RNA (ribonucleic acid), DNA (deoxyribonucleic acid), or a recombinant gene such as an expression vector into which RNA or DNA has been integrated.

Low molecular agent includes a neurotransmitter, which includes amines such as acetylcholine, adrenaline, noradrenalin, dopamine, serotonin, and amino acids such as glutaminic acid, glycine and gamma-amino butyrate.

According to the present invention, an active ingredient can be used alone or in combination with one or more other active ingredients.

Collagen which is used as a carrier is a protein which is widely found in various animal including invertebrate and vertebrate, which occupies about one-third of total amount of protein of mammal. The recent studies have revealed that there are many kind of collagens, and molecular species from type I to type XVI are known. Collagen to be used for the formulation of the present invention is preferably type I collagen derived from a mammal, although there is no limitation in the origin and molecular species of collagen. Collagen has been already used for suture or the like, and its safety is known by those skilled in the art. However, higher safety may be achieved by using atelocollagen in the invention, antigenicity of which is very lowered by removing a major antigenic moiety, i.e. telopeptide. Small amount of other component such as gelatin may also be included therein.

A method of preparation of the present invention comprises, but not limited to, for example, lyophilizing mixed solution in water containing an active ingredient, collagen and glycosaminoglycan, pulverizing the resultant mixture, and then, putting the resultant mixture into a mold for compression molding to give a solid formulation.

The formulation thus obtained can be molded in the form suitable for administration route and site, such as needle, rod, concentric circle, disc, and film-shaped forms. The formulation can also be prepared by a method comprising kneading together the pulverized mixture, which consists of an active ingredients collagen and glycosaminoglycan, or other additive, with an appropriate quantity of water or buffer, which is then molded to needle or stick-shaped form, followed by drying again.

Collagen has a nature of forming fiber under neutral condition, thereby it becomes insoluble. Since, however, it exists as a solution under acidic condition, mixing of an active ingredient and glycosaminoglycan can be easily conducted in a solution. There is no limitation on the order of mixing thereof An appropriate amount of pharmaceutically acceptable additive may also be added, if such addition is needed, during the preparation of the formulation.

A method of administration of the present formulation includes, but not limited to, parenteral administration, especially, direct administration in the form of solid in the body such as by injection, insertion, implantation, indwelling during an operation, which is expected to produce a superior efficacy. The formulation molded in the form of film or seat can also be applied directly to an affected site, and can be used as an external agent as well as an internal agent. Thus, the formulation of the invention can be formed in various forms and can be administered with various methods. Depending on the expected effect, the formulation can be systemically or topically administered.

The sustained release formulation of the present invention is very useful because it can control sustained release of an active ingredient depending on the type and amount of glycosaminoglycan contained therein, which allows to treat human or livestock's pathological condition. In addition, both of collagen and glycosaminoglycan are a substance derived from organisms and superior in biodegradability after an active ingredient is released from the formulations and therefore, the formulation is a superior pharmaceutical formulation with high safety.

BRIEF DESCRIPTION OF THE DRAWINGS

FIG. 1 shows that scanning electron microscopic photograph of crystal structure of collagen in the formulations containing chondroitin sulfate (1-B) or not (1-A).

FIG. 4 shows morphology of the inner part of the formulation which contains 5% of chondroitin sulphate (a), hyaluronic acid (b), heparin (c), heparan sulfate (d)y dermatan sulfate (e)r or keratan sulfate (f).

EXAMPLES

Figure 2:
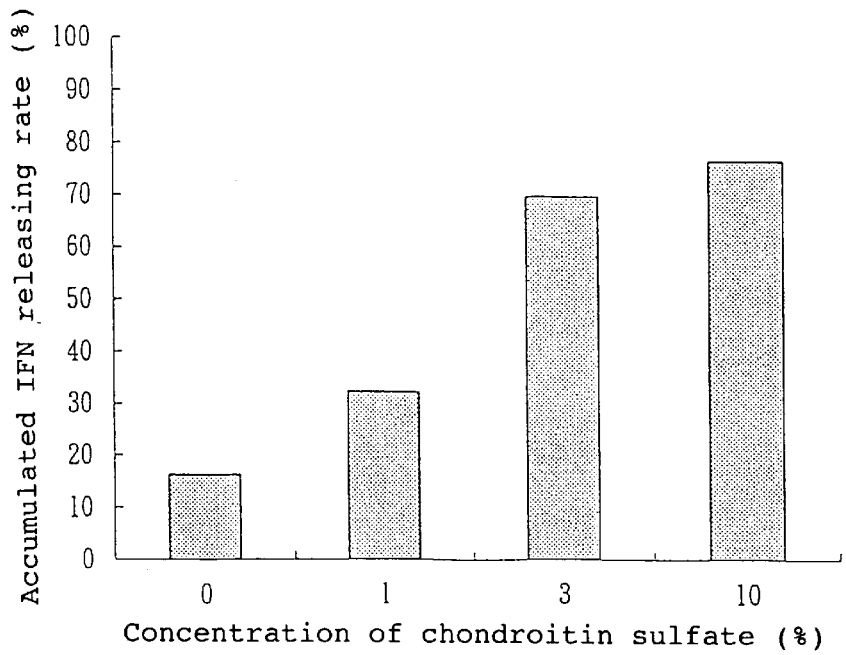
FIG. 2 is a graph showing the result of in vitro release test for the formulation obtained in Reference Example 1, and Examples 1, 2 and 3. Accumulated release amount was calculated from the amount of IFN released from the formulation for 7 days, and the accumulated release amount was divided by the amount of IFN kneaded in the formulation to give an accumulated release rate.

The present invention is illustrated in more detail in the following References, Examples and Experiments which are not intended to limit the scope of the invention Percent (%) as used hereinafter means % by weight unless otherwise mentioned.

Reference 1

A 2% (w/v) atelocollagen solution and a solution including alpha-interferon as an active ingredient are mixed and then the mixture is lyophilized. To the lyophilized product, an appropriate quantity of distilled water is added, and the resultant mixture is kneaded, put into a syringe, extruded therefrom, and dried to give a cylindrical formulation containing 10 million international units (10 MIU) of alpha-interferon per formulation.

Reference 2

A 2% (w/v) atelocollagen solution and a solution including lysozyme as an active ingredient are mixed and then the mixture is lyophilized. To the obtained lyophilized product, an appropriate quantity of distilled water is added, and the resultant mixture is kneaded, put into a syringes extruded therefrom, and dried to give a cylindrical formulation containing 6.7% (by weight) lysozyme per formulation.

Example 1

To a 2% (w/v) atelocollagen solution, a chondroitin 6-sulfate solution is added, and an alpha-interferon solution is admixed thereto, and the mixture is lyophilized. To the obtained lyophilized product, an appropriate quantity of distilled water is added and the resultant mixture is kneaded, extruded, and then dried to give a cylindrical formulation containing 10 MIU alpha-interferon and 1% (by weight) chondroitin sulfate per formulation.

Example 2

To a 2% (w/v) atelocollagen solution, chondroitin 6-sulfate solution is added, and an alpha-interferon solution is admixed thereto, and the mixture is lyophilized. To the obtained lyophilized product, an appropriate quantity of distilled water is added and the resultant mixture is kneaded, extruded, and then dried to give a cylindrical formulation containing 10 MIU alpha-interferon and 3% (by weight) chondroitin sulfate per formulation.

Example 3

To a 2% (w/v) atelocollagen solutions chondroitin 6-sulfate solution is added, and an alpha-interferon solution is admixed thereto, and the mixture is lyophilized. To the obtained lyophilized product, an appropriate quantity of distilled water is added, and the resultant mixture is kneaded, extruded, and then dried to give a cylindrical formulation containing 10 MIU alpha-interferon and 10% (by weight) chondroitin sulfate per formulation.

Example 4

To a 2% (w/v) atelocollagen solution, chondroitin 6-sulfate solution is added, and a lysozyme solution is admixed thereto, and the mixture is lyophilized. To the lyophilized product, an appropriate quantity of distilled water is added, and the resultant mixture is kneaded, extruded, and then dried to give a cylindrical formulation containing 6.7% (by weight) lysozyme and 3% (by weight) chondroitin sulfate per formulation.

Example 5

To a 2% (w/v) atelocollagen solution, heparin is added, and a lysozyme solution is admixed thereto, and the mixture is lyophilized. To the lyophilized products an appropriate quantity of distilled water is added, and the resultant mixture is kneaded, extruded, and then dried to give a cylindrical formulation containing 6.7% (by weight) lysozyme and 3% (by weight) heparin per formulation.

Example 6

To a 2% (w/v) atelocollagen solution, chondroitin 6-sulfate solution is added, and an alpha-interferon solution is admixed thereto, and the mixture is lyophilized. To the lyophilized product, an appropriate quantity of distilled water is added and the resultant mixture is kneaded. Then, by using a nozzle having a double-structure, the mixture was extruded together with a kneaded collagen solution which was separately prepared, and the product was then dried to give a concentric circular formulation, of which the outer layer was coated with collagen.

Example 7

To a 2% (w/v) atelocollagen solution, either chondroitin 6-sulfate solution, hyaluronic acid solution, heparin solution, heparan sulfate solution, dermatan sulfate, or keratan sulfate solution was added. The resultant mixture is lyophilized. To the lyophilized product, an appropriate quantity of distilled water is added and the resultant mixture is kneaded, extruded, and then dried to give a cylindrical formulation containing 5% (by weight) chondroitin sulfate, hyaluronic acid, heparin, heparan sulfate, dermatan sulfate, or keratan sulfate.

Examination 1

A formulation comprising collagen with or without 10% chondroitin 6-sulfate was morphologically examined by scanning electron microscopy. The test result was shown in FIG. 1.

The formulation without chondroitin sulfate (1-A) has thick fiber bundles of collagen which are orientated along with the extruded direction. On the other hand, when the formulation contains chondroitin sulfate, collagen fiber becomes thinner and is tangled at random each other to form mesh (1-B).

Examination 2

Using formulations as prepared in Reference Example 1, and Examples 1, 2 and 3, in vitro release test of IFN was performed in a PBS+0.3% Tween 20 solution. As shown in FIG. 2, the amount of IFN released from the formulation increased according to the increase of the amount of chondroitin sulfate added.

Examination 3

Figure 3:
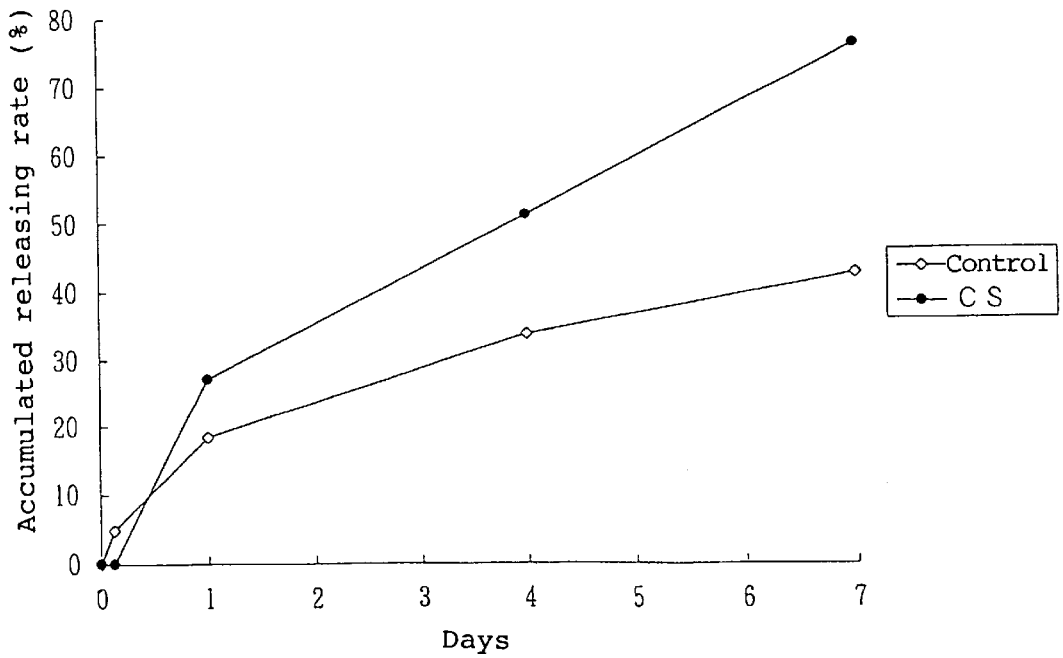
FIG. 3 shows the results of in vitro release test by using the formulations prepared in Reference Example 2 (control) and Example 4 (CS).

Release test of lysozyme formulations-as obtained in Reference Example 2 and Example 4 was conducted under the same conditions as used in Examination 2. The result was provided in FIG. 3.

Chondroitin-free containing formulation (control) showed time-dependent decrease of release rates and the accumulated release of lysozyme for 7 days was 40%. On the other hand, the formulation containing 3% chondroitin sulfate showed continued drug release at a certain rate without decrease of the release rates and the accumulated release of lysozyme for 7 days was about 80%.

Examination 4

In the manner as described in Examination 1, a formulation containing 5% of glycosaminoglycan, which was obtained in Example 7, was morphologically examined by scanning electron microscopy The results are given in FIG. 4. In the formulations containing hyaluronic acid (b), heparin (c); heparan sulfate (d), dermatan sulfate (e), or keratan sulfate (f) as well as the formulation containing chondroitin sulfate (a), the formation of mesh which is at random tangled each other was observed.

We claim:

1. A sustained release formulation containing a therapeutically active ingredient and collagen as a drug carriers which is characterized by additionally containing glycosaminoglycan as an additive.

2. The sustained release formulation as claimed in claim 1 wherein said glycosaminoglycan is selected from the group consisting of chondroitin sulphate, hyaluronic acid, heparin, heparan sulfates dermatan sulfates or keratan sulfate.

3. The sustained release formulation as claimed in claim 1 wherein said glycosaminoglycan is chondroitin 6-sulfate.

4. The sustained release formulation as claimed in claim 1 wherein said glycosaminoglycan is heparin.

5. The sustained release formulation as claimed in any one of claims 1 to 4 wherein the therapeutically active ingredient is protein, peptide, glycoprotein, polysaccharide, or gene having a physiological activity.

6. The sustained release formulation as claimed in any one of claims 1 to 4, wherein a content of the glycosaminoglycan is less than 40%, by weight of the formulation.

7. The sustained release formulation as claimed in any one of claims 1 to 4, wherein a content of the glycosaminoglycan is 1–10%, by weight of the formulation.

8. The sustained release formulation as claimed in any one of claims 1 to 4, wherein a content of the collagen is 20–95%, by weight of the formulation.

9. The sustained release formulation as claimed in any one of claims 1 to 4, wherein a content of the collagen is 75–91%, by weight of the formulation.

10. The sustained release formulation as claimed in any one of claims 1 to 4, wherein a content of the glycosaminoglycan is less than 40% and a content of the collagen is 20–95%, by weight of the formulation.

11. The sustained release formulation as claimed in any one of claims 1 to 4, wherein a content of the glycosaminoglycan is 1–10% and a content of the collagen is 20–95%, by weight of the formulation.

12. The sustained release formulation as claimed in any one of claims 1 to 4, wherein a content of the glycosaminoglycan is less than 40% and a content of the collagen is 75–91%, by weight of the formulation.

13. The sustained release formulation as claimed in any one of claims 1 to 4, wherein a content of the glycosaminoglycan is 1–10% and a content of the collagen is 75–91%, by weight of the formulation.

* * * * *